United States Patent [19]

LeVantine

[11] 4,281,616
[45] Aug. 4, 1981

[54] AUTOMATIC FINGERPRINT CARD HOLDER

[76] Inventor: Allan D. LeVantine, 18225 Rancho St., Tarzana, Calif. 91356

[21] Appl. No.: 207,655

[22] Filed: Nov. 17, 1980

Related U.S. Application Data

[63] Continuation-in-part of Ser. No. 90,875, Nov. 2, 1979, abandoned.

[51] Int. Cl.³ .............................. B41K 1/00; A61B 5/10
[52] U.S. Cl. .................................. 118/31.5; 118/500; 118/503; 427/1
[58] Field of Search ...................... 118/31.5, 500, 503; 427/1

[56] References Cited
U.S. PATENT DOCUMENTS

| 2,629,194 | 2/1953 | Johnson et al. | 118/31.5 |
| 3,824,951 | 7/1974 | LeVantine et al. | 118/31.5 |

Primary Examiner—Michael R. Lusignan

[57] ABSTRACT

A fingerprint card holding device that simplifies the procedure for taking fingerprint impressions on fingerprint cards. The device includes a platen means upon which the card is placed, a hoop means for holding the card to the platen means, an indexing means for locating the card in the correct positions and an actuating means for moving the card for rolling the prints of the fingers of the right hand, the fingers of the left hand and for making the flat fingerprints of both hands.

16 Claims, 10 Drawing Figures

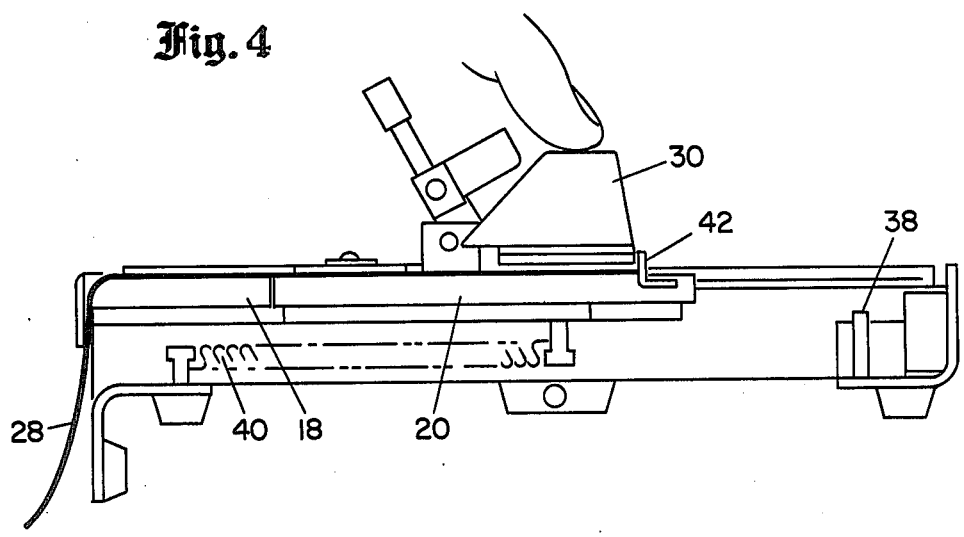
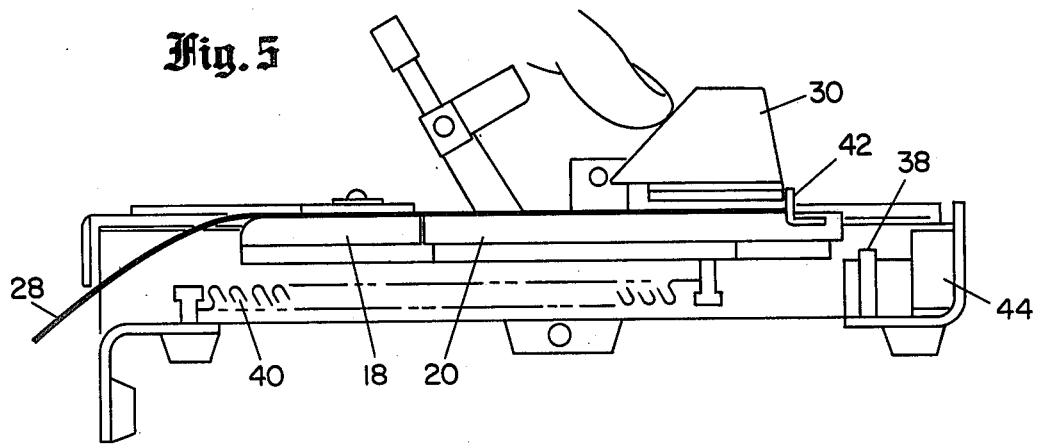
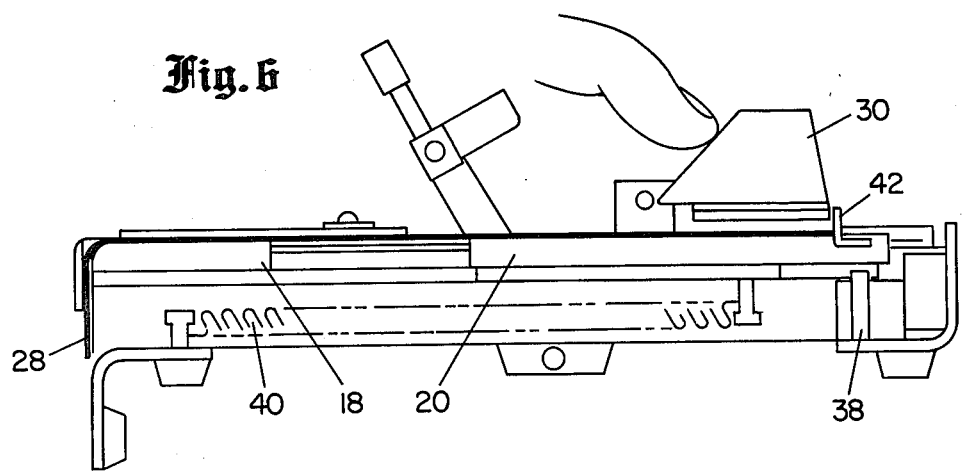

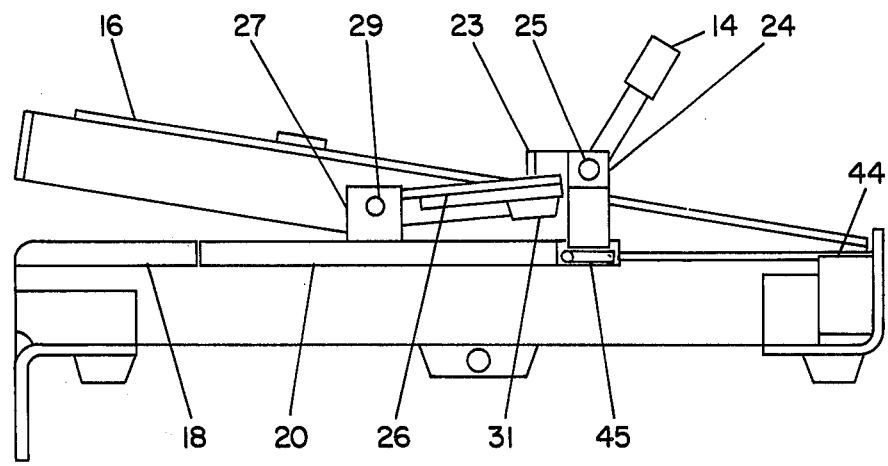
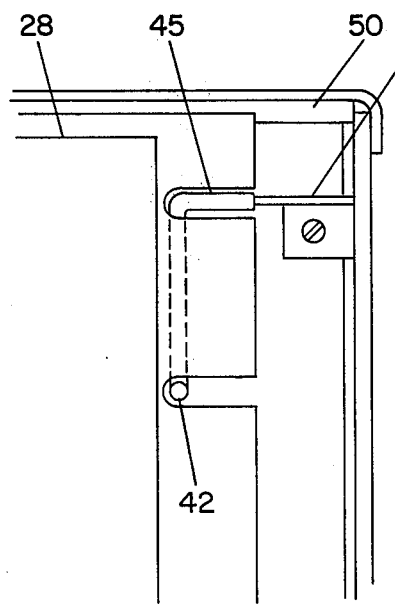
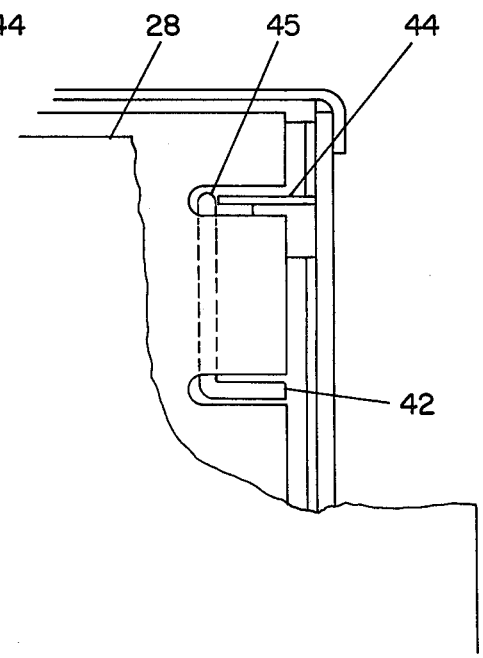

AUTOMATIC FINGERPRINT CARD HOLDER

This is a continuation in part of application Ser. No. 90,875, filed Nov. 2, 1979, now abandoned.

This invention relates to the holding and positioning of a fingerprint card and, more specifically, to an apparatus for automatically holding and positioning the card in the correct locations which are indicated on the card for (1) rolling the fingerprints of the right hand, (2) rolling the fingerprints of the left hand and (3) for making the flat fingerprints of both hands.

The print art card holder has been a standard since the inception of fingerprinting for police and identification work. It consists of a block of wood with a radius on the front edge. A metal hoop is attached near the rear of the block and hinged so that it can be lowered over the front of the block. In use, the hoop is raised, the fingerprint card is inserted under the hoop to an estimated position for rolling prints of the fingers of the right hand, and the hoop is lowered. Lowering the hoop bends the card downward over the radius on the block so that the fingerprints can be placed on the indicated locations on the card. The card is then observed to ascertain if it is in the correct location. If not, the hoop must be raised and the card relocated. This operation is repeated again, for a second indicated location on the card, for the fingerprints of the left hand, and a third time to move the card to the location for making flat prints of all ten fingers.

This prior art has the disadvantage that it requires human judgement to properly position the card at each indicated location. Hence, many times the card must be readjusted to place it in the correct location. In some cases, the prints may be improperly located resulting in rejection by a central agency as unsuitable for classification and/or storage.

An investigation of the literature as well as interrogation of persons of stature in the identification field has failed to reveal any evidence of a fingerprint card holding device that embodies the features or principles claimed for this invention. Moreover, this invention was conceived as the result of the suggestion of a very senior fingerprint technician, of long standing in the field, who stated that there had been nothing new developed in a fingerprint card holder in over fifty years.

It is, accordingly, an objective of the present invention to provide an improved fingerprint card holding apparatus.

It is another objective of the invention to provide an apparatus that positions the fingerprint card such that the fingerprints can be properly placed in the indicated locations on the card.

It is yet another objective of the invention to provide a means by which the fingerprint card is moved to a new position and folded downward over a radius so that the unused portion of the card does not interfere with rolling the fingerprints.

It is also an objective of the invention to provide a card holding apparatus such that once a fingerprint card is inserted it does not have to be manually touched by the operator until the card is completely filled with prints and ready for removal from the apparatus.

Briefly stated, and in accord with the presently preferred embodiment of the invention, a card holding apparatus is provided which includes two coupled platens, (a front platen and a rear platen), on which the card is supported with guides and stops which align and limit the distance the card can be inserted, a clamp bar which holds the card to the platens, a hoop which folds the card down over the front of the platen, a lever means for actuating the hoop, a sliding means by which the platens can be moved to bring the card to a new position, stop means which limits the motion of the platen to coincide with the indicated positions on the card, and a card folding means involving the front platen which permits the card to be relocated to a new position and then causes it to be folded down.

For a complete understanding of the invention together with an appreciation of other objectives and advantages thereof, please refer to the attached drawings and the following description of the drawings in which:

FIG. 4 is the cross section of FIG. 3 wherein the fingerprint card has been locked in its first position as the result of the downward motion of the hoop.

FIG. 5 is the cross section of FIG. 3 showing the fingerprint card being advanced to the next position by the motion and force of the operator's finger.

FIG. 6 is the cross section of FIG. 3 showing the fingerprint card folded down as the result of the motion of the front platen.

FIG. 7 is identical to FIG. 4 except that the card is locked in its second position.

FIG. 8 is a cross-section in accordance with the invention through the region of the card stop latch 24 lever arm 45 of toggle assembly 46 and rear platen stop 44.

FIG. 9 is a plan view of a portion of the rear platen showing the interaction of toggle arm 45 and rear platen stop 44 with the card in the first position, which follows from FIG. 5, and the platen forced to its rearmost position.

Figure 7:
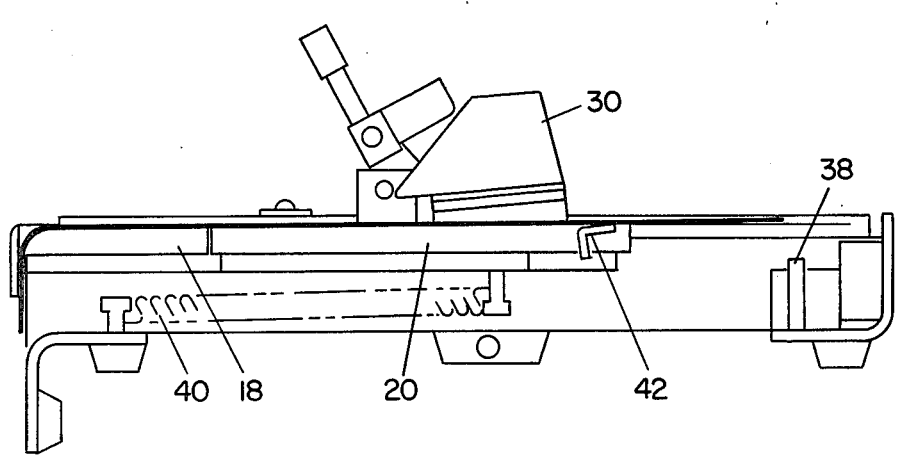
FIG. 7 is the cross section of FIG. 3 showing the rear platen returned to join the front platen completing the full cycle of advancing the card.

FIG. 10 is similar to FIG. 9 with the card in the second position, which follows from FIG. 7, and with the platen forced to its rearmost position.

Figure 1:
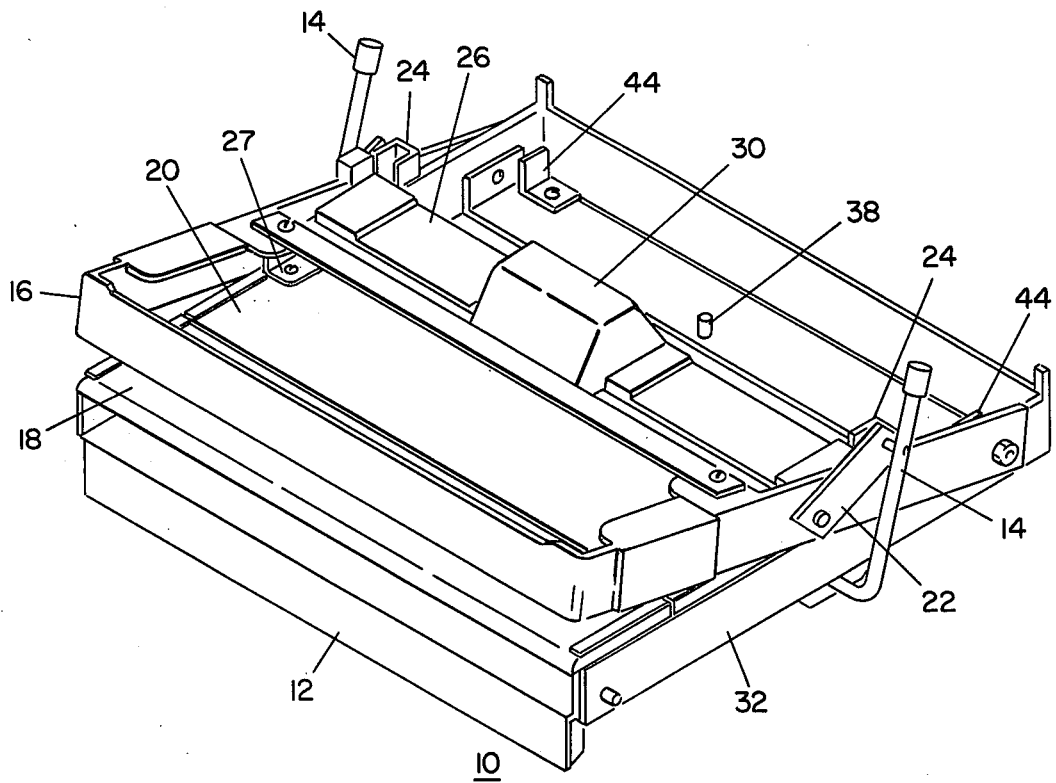
FIG. 1 is a perspective view of an embodiment of the invention showing the card holder, with the hoop raised, ready for insertion of a card.

The embodiment of the invention of FIG. 1 is envisioned for use on a ledge or counter top, as are prior art card holders. The card holder 10 has rubber feet 13 to prevent it from sliding on the ledge or counter top and an apron 12 which projects downward below the edge of the ledge or counter top to prevent it from moving in a rearward direction as the result of rearward forces being applied to actuate the apparatus.

In preparation for receiving a fingerprint card, the lever 14 is positioned to the rear. In so moving, it raises the forward portion of the hoop 16 about its pivots 17 above the plane of the front and rear platens 18 and 20 by means of connecting links 22 and lever tie bar 49. At the same time the card stop latches 24 snap over the clamp bar 26 momentarily depressing it against the force of a spring (not shown) and allowing the clamp bar to snap up again. Card stop latches 24 are pivoted on pins 25 which connect links 22 to levers 14 and are held in an upward position perpendicular to lever 14, when lever 14 is in the forward position, by means of a torsion spring (not shown) mounted about pin 25. As lever 14 is moved to the rear position, latches 24 contact the upper surface of clamp bar 26 which forces clamp bar 26 downward momentarily and allows it to snap up again as they pass to the rear of the clamp bar. As the hoop 16 rises, as the result of the rearward motion of the levers 14, it intersects that portion 23 of the latches 24, which are forward of pivots 25, forcing the latches to rotate about pivot 25 and hence into the downward position, as shown in FIG. 8. Once the clamp bar 26 has snapped up, into the upward position, the levers 14 are locked in the rearward position and the hoop 16 is locked in the up position by reason of the interference as the result of clamp bar 26 being in the motion path of the pivot 25 which is affixed to lever 14.

When the card stop latches 24 are in the downward position they project into the slots in rear platen 20, in which arms 45 of toggle assemblies 46 are located, and hence project below the upper surface of rear platen 20. When the latches 24 are in this position they form a barrier, or fence, which prevents a fingerprint card from being inserted beyond their location. Thus, the card stop latches serve to locate the fingerprint card, on initial insertion into the card holder, and in this embodiment of the invention have been arranged so as to provide proper alignment for printing the fingers of the right hand as the first position in utilization of the card holder. The fingerprint card can now be inserted.

Figure 3:
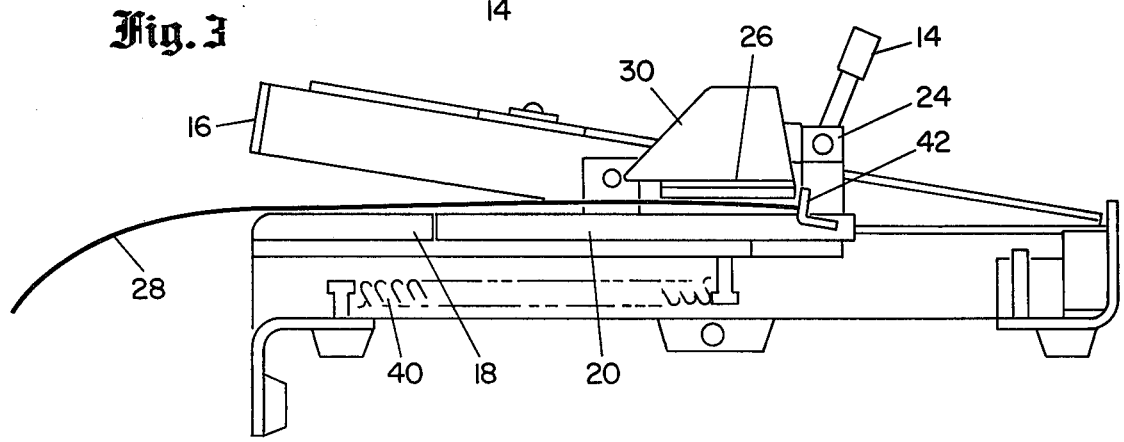
FIG. 3 is a cross section in accordance with the invention with a fingerprint card being inserted into the card holder.

The card 28, FIG. 3, is then inserted under the hoop 16, over the platens 18 and 20 and under the clamp bar 26 until it hits the card latch stops 24 which are now in the down position. The clamp bar 26 is then depressed by pressing downward on the actuator knob 30 which is mounted on the clamp bar. Clamp bar 26 is hinged on pivots 29 affixed to brackets 27, which are integral with rear platen 20. Clamp bar 26 has two rubber feet 31 mounted on the underside near its lateral limits. When the clamp bar is depressed it holds the fingerprint card tightly against the platen. Hence, when knob 30 is depressed, it clamps the card in place on the platen. Also, as clamp bar 26 is depressed it moves below the path of motion of pivots 25 and hence releases the card stop latches 24 and the hoop lever 14. The hoop lever 14 is now forced forward by means of a torsion spring (not shown) which in turn brings down the hoop 16 by means of connecting links 22 forcing the card 28 to bend downward over the front of the card holder as shown in FIG. 4. The hoop lever 14 and the link 22 are of such an arrangement that the lever is in an "over center" position with respect to the pivots of the link when the hoop 16 is down and the lever is in the forward position. This arrangement produces maximum force to bend the card 28 down and also locks the hoop 16 in the down position. The card 28 is now in position for taking the first set of rolled prints (those from the right hand).

Figure 2:
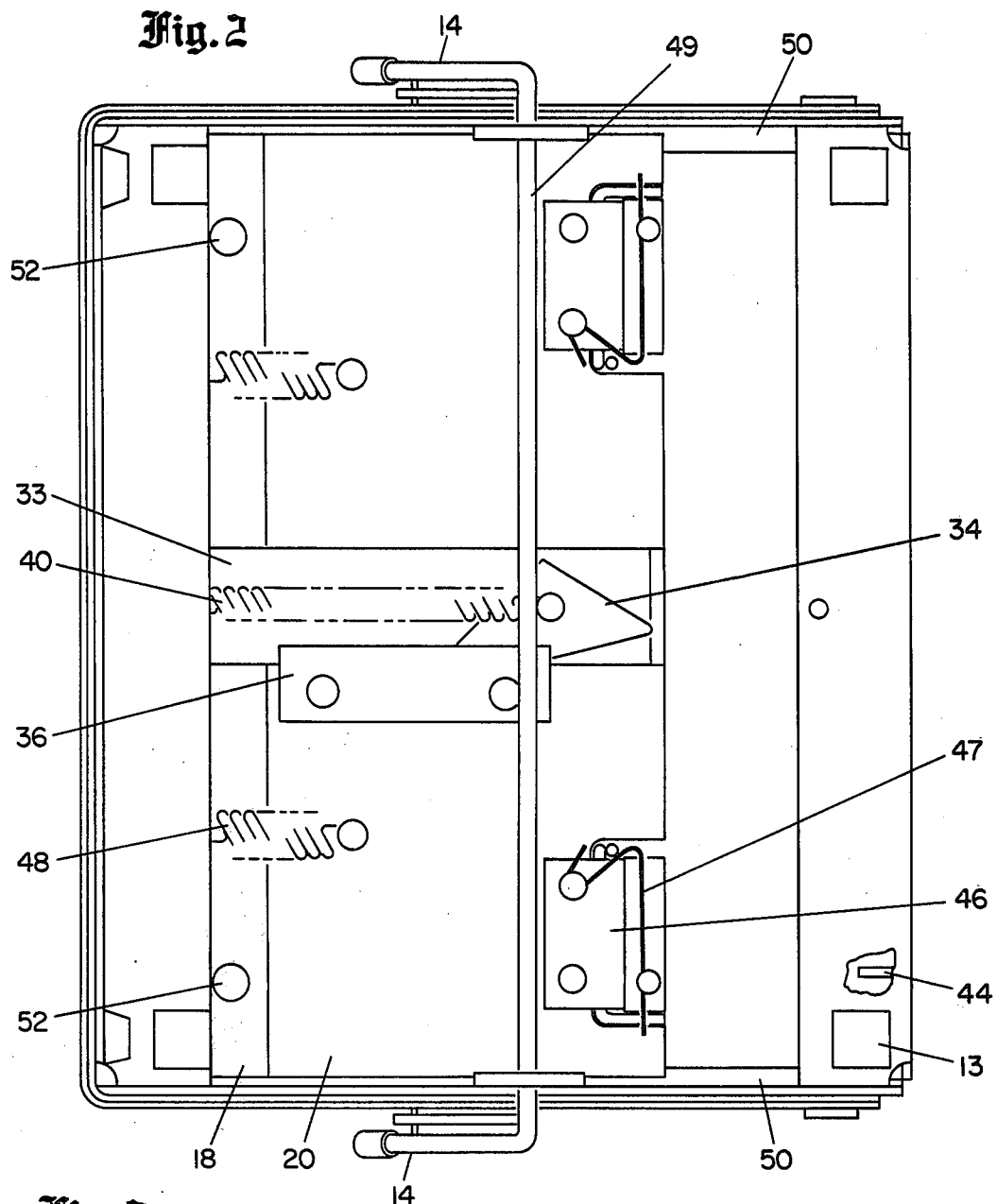
FIG. 2 shows the underside of the card holder in accordance with the invention.

To move the card to the second position (for taking a rolled set of prints from the left hand), the operator presses his thumb or finger in a rearward direction against the forward surface of the actuator knob 30 as shown in FIG. 5 and the knob is forced in a rearward direction. This action forces the clamp bar 26, which is pivoted on brackets 27 mounted on the rear platen 20, downward against the card 28 locking it by friction to the rear platen 20 by means of rubber feet 31, and then carries the rear platen 20 in a rearward direction. Platen 20 is grooved on its sides so that it is retained in the frame 32 by tracks 50, which fit into the grooves, and permit movement of the platen in the forward and rearward directions as it slides along tracks 50 in the main frame 32. The front platen 18, which is also grooved on its edges to fit on tracks 50, is also carried rearward along tracks 50 by this action as it is latched to the rear platen 20 by means of an extension 33, FIG. 2, on the front platen and a mechanical latch 34 which couples to latch plate 36 on the rear platen. Thus, the card and the two platens are moved rearward as a unit as shown in FIG. 5. And, because the front platen 18 has been moved rearward from its position of contact with the card 28, the card is free to be drawn under the edge of the hoop 16 at the front of the card holder 10.

The platens 18 and 20 and card 28 move rearward until the front platen latch 34 contacts the front platen release post 38 forcing latch 34 to rotate on its mounting post 35 on front platen extension 33. Such rotation moves latch 34 out of notch 37 on latch plate 36 releasing the front platen 18 from the rear platen 20. The front platen 18 then moves forward in tracks 50 driven by the force of the front platen return spring 40. The rear platen, still under the action of the rearward force on the actuator knob 30, continues rearward a short distance until, as shown in FIG. 9, the lever arms 45 of toggle assembly 46 hit the rear platen stops 44 which are axially in line with lever arms 45. Simultaneously the front platen 18 continues forward lifting up the forward end of card 28 and clamping it against the hoop 16 as shown in FIG. 6. The clamp bar 26 is then released which unclamps the card 28 from the rear platen 20. The rear platen 20 thus moves forward on tracks 50 to its original position by means of a force applied by the rear platen return springs 49, FIG. 2, and latches to the front platen 18 in the forward position as latch 34 re-engages latch plate 36 by means of a torsion spring (not shown) about post 35. The fingerprint card is now in the second position as shown in FIG. 7.

When the card 28 is in the second position as shown in FIG. 7 it projects under the clamp bar 26 and passes over the lever arms 42 of toggle assembly 46 which are spring-loaded in the UP position by means of springs 47 which press against the connected levers 45 of the toggles. The force of the card overcomes the force of springs 47 and holds the levers 42 in a horizontal position and forces the lever arms 45 into a downward position as shown in FIG. 7. This action prevents the lever arms 45 of the toggle assemblies 46 from hitting the rear platen stops 44 when the platen 20 is sliding rearwards. This permits the platen 20 to carry the card further rearward, when it is moved rearward, as the platen stops 44 now enter the slots in the rear platen 20, which were previously occupied by the lever arms 45, as shown in FIG. 10 where card 28 has been cut away to show the toggle assembly. This extra distance is necessary to provide greater sliding motion to properly locate the card 28 because of the larger spacing required for making the flat impressions of the third position, which is approximately ½ inch greater than the spacing on the card required for the first or second positions.

To physically move the card 28 to the third position the procedure is the same as for moving the card from the first position, FIG. 4 to the second position, FIG. 6. The actuator knob 30 is simply pushed to the rear as far as it will go and then released for each additional change of the card 28. When all the prints have been made on the card 28, it may now be removed from the rear of the card holder 10. The card 28 is simply grasped at the rear end which now projects beyond the rear of the card holder and manually pulled rearward until it clears the clamp bar 26 and is then lifted out.

While the principles of the invention are thus disclosed and one embodiment described in detail, it is not intended that the invention be limited to this embodiment. It is recognized that many modifications will occur to those skilled in the art which lie within the spirit and scope of the invention. It is intended that the invention cover such modifications and be limited in scope only by the appended claims.

What is claimed is:

1. An apparatus for holding a fingerprint card that locates the fingerprint card in the proper positions for taking a full set of rolled and flat fingerprints, comprising:
    a platen;
    a means for locating and retaining a fingerprint card on the platen;
    a frame for supporting the platen;
    a slide means on the frame that permits the platen to be advanced to carry the fingerprint card to the proper positions;
    an actuator means for advancing the platen to the proper positions;
    an indexing means for stopping the advance of the platen at the next proper position;
    a hoop means for folding the fingerprint card down over the front of the apparatus;
    a lever means for actuating the hoop;
    a clamping means that frees the fingerprint card as it is advanced to the next position and then folds the card down and locks it at that position;
    a restraining means that prevents the apparatus from moving when the fingerprint card is being advanced.

2. The apparatus of claim 1 wherein a clamp bar is supported and pivoted off the platen, said clamp bar containing an actuator knob, such that when the actuator knob is forced toward the rear of the apparatus, it clamps the fingerprint card to the platen such that the fingerprint card moves with the platen.

3. The apparatus of claim 1 wherein the hoop means is actuated by a pivoted lever, connected to the hoop means by a link, in such a manner that when the hoop is lowered the lever and the link pivots are aligned so that the hoop is locked in the lowered position.

4. The apparatus of claim 1 wherein the hoop means is actuated by a pivoted lever, connected to the hoop means by a link, in such a manner that when the hoop is raised by the lever the lever is latched over the clamp bar such that the hoop is locked in the raised position.

5. The apparatus of claim 4 wherein the lever is released from locked position when the clamp bar is depressed.

6. The apparatus of claim 4 wherein the lever is spring loaded by a torsion spring such that the hoop is forced into the lowered position when the lever is released.

7. The apparatus of claim 4 wherein a card stop means is actuated by the lever when it is in the raised position such that it limits the distance a card can be inserted into the apparatus.

8. The apparatus of claim 1 wherein the platen is composed of two coupled portions, a front platen and a rear platen.

9. The apparatus of claim 8 wherein the front platen is connected to the rear platen by a latch means.

10. The apparatus of claim 8 wherein the front platen and the rear platen are individually attached to the frame of the apparatus by springs such that when they are translated in a rearward direction they will return by the spring force to the front-most position of the apparatus when released.

11. The apparatus of claim 10 wherein a release means on the frame will unlatch the front platen from the rear platen, at a specified rearward location, such that the front platen will separate from the rear platen and return by spring force to its frontmost position as the platens are moved rearward.

12. The apparatus of claim 11 wherein a fingerprint card is released from its folded down position and carried rearward as the platens are moved rearward.

13. The apparatus of claim 11 wherein a fingerprint card is clamped into a folded down position by the forward moving front platen after it is released from the rear platen.

14. The apparatus of claim 1 wherein a lever means is depressed by the fingerprint card permitting the platen to travel an additional rearward distance to coincide the positioning of the card with the non-uniform spacing for placing the fingerprints on the card.

15. The apparatus of claim 1 wherein the restraining means consists of an apron projecting downward from the front of the frame below the counter or ledge on which the apparatus is located.

16. The apparatus of claim 1 wherein once a fingerprint card is inserted into the apparatus a series of operations is performed upon it by the apparatus moving it to all positions where it is indicated fingerprints are to be located on it.

* * * * *